US005475159A

United States Patent [19]

Singleton et al.

[11] Patent Number: 5,475,159
[45] Date of Patent: Dec. 12, 1995

[54] PROCESS FOR THE DIRECT HYDROGENATION OF METHYL ESTERS

[75] Inventors: David M. Singleton; Brendan D. Murray, both of Houston, Tex.

[73] Assignee: Shell Oil Company, Houston, Tex.

[21] Appl. No.: 335,018

[22] Filed: Nov. 7, 1994

[51] Int. Cl.$^6$ .................... C07C 29/136; C07C 29/141
[52] U.S. Cl. .................... 568/864; 568/861; 568/884; 568/885
[58] Field of Search .................... 568/861, 864, 568/884, 885

[56] References Cited

U.S. PATENT DOCUMENTS

| | | | |
|---|---|---|---|
| 4,380,657 | 4/1983 | Slaugh | 549/509 |
| 4,417,000 | 11/1983 | Slaugh | 518/713 |
| 4,565,803 | 1/1986 | Schoenthal et al. | 502/303 |
| 4,728,671 | 3/1988 | Hinnekens | 549/503 |
| 4,851,593 | 7/1989 | Gilbert et al. | 568/864 |
| 5,001,284 | 3/1991 | Dupont | 568/885 |
| 5,043,485 | 8/1991 | Fleckenstein et al. | 568/885 |
| 5,120,700 | 6/1992 | Matsuda et al. | 502/329 |
| 5,124,491 | 6/1992 | Fleckenstein et al. | 568/885 |
| 5,142,067 | 8/1992 | Weyman et al. | 549/326 |
| 5,155,086 | 10/1992 | Thakur et al. | 502/342 |
| 5,157,168 | 10/1992 | Wilmott et al. | 568/877 |
| 5,180,858 | 1/1993 | Fleckenstein et al. | 568/885 |
| 5,233,099 | 8/1993 | Tabata et al. | 568/885 |
| 5,233,100 | 8/1993 | Tabata et al. | 568/885 |
| 5,254,520 | 10/1993 | Sofianos | 502/307 |
| 5,334,779 | 8/1994 | Kuo | 568/864 |
| 5,345,005 | 11/1994 | Thuruv et al. | 568/885 |
| 5,364,986 | 7/1985 | Demmering | 568/885 |
| 5,387,753 | 2/1995 | Scarlett et al. | 568/864 |
| 5,395,990 | 3/1995 | Scarlett et al. | 568/864 |
| 5,395,991 | 3/1995 | Scarlett et al. | 56/864 |

FOREIGN PATENT DOCUMENTS

| | | |
|---|---|---|
| 0424069A1 | 4/1991 | European Pat. Off. . |
| 0523818A2 | 1/1993 | European Pat. Off. . |

*Primary Examiner*—Werren B. Lone
*Attorney, Agent, or Firm*—Pamela J. McCollough

[57] ABSTRACT

This invention relates to a process for the direct hydrogenation of methyl esters which comprises contacting and reacting one or more detergent range methyl esters with hydrogen under predominantly liquid phase hydrogenation conditions in the presence of a catalyst comprising a copper compound, a zinc compound, and at least one compound selected from the group consisting of aluminum, zirconium, magnesium, a rare earth and mixtures thereof.

20 Claims, No Drawings

PROCESS FOR THE DIRECT HYDROGENATION OF METHYL ESTERS

FIELD OF THE INVENTION

This invention relates to a process for the direct hydrogenation of detergent range methyl esters in a predominantly liquid phase utilizing a catalyst comprising a copper compound, a zinc compound, and at least one compound selected from the group consisting of aluminum, zirconium, magnesium, a rare earth and mixtures thereof.

BACKGROUND OF THE INVENTION

The hydrogenation of carboxylic acids and carboxylic esters to alcohols is known in the art, and various methods and catalysts have been suggested for effecting the hydrogenation. A commonly practiced method involves the use of a copper-chromite-based hydrogenation catalyst. While copper chromite catalysts are successful and commercially available, the disposal of the spent copper chromite catalyst is a problem since chromium can exist in different oxidation states. Some of these oxidation states are reported to be toxic to humans.

SUMMARY OF THE INVENTION

This invention therefore provides a process for the direct hydrogenation of esters which comprises contacting and reacting one or more detergent range methyl esters with hydrogen under predominantly liquid phase hydrogenation conditions in the presence of a catalyst comprising a copper compound, a zinc compound, and at least one compound selected from the group consisting of aluminum, zirconium, magnesium, a rare earth and mixtures thereof. The catalyst composition is prepared by a process which comprises co-precipitating from aqueous solution compounds of copper, zinc and at least one of aluminum and/or zirconium and/or magnesium and/or rare earth, washing, drying and calcining the precipitate, and subsequently activating the calcined precipitate in a reducing atmosphere.

It has been found that high purity alcohols can be obtained utilizing a catalyst comprising a copper compound, a zinc compound, and at least one rare earth compound.

DESCRIPTION OF THE PREFERRED EMBODIMENTS

The present invention relates to a process for the direct hydrogenation of detergent range methyl esters to form fatty alcohols. As used herein, the term "detergent range methyl esters" refers to compounds, typically $C_6$ to $C_{22}$ compounds, which have been produced by ester exchange of natural oils, such as coconut oil, rape seed oil, and palm oils. Examples of detergent range methyl esters include methyl decanoate (methyl caprate), methyl dodecanoate (methyl laurate), methyl tetradecanoate (methyl myristate), methyl hexadecanoate (methyl palmitate), methyl octadecanoate (methyl stearate), and methyl octadecenoate (methyl oleate). As used herein, "fatty alcohol" refers to an alcohol, preferably a linear alcohol, containing from about 6 to about 22 carbon atoms, preferably from about 10 carbon atoms to about 22 carbon atoms. Typical fatty alcohols produced by the direct hydrogenation process of the present invention include decanol, dodecanol, tetradecanol, hexadecanol, octadecanol, and the like, and mixtures thereof.

The catalyst compositions of the present invention comprise mixtures of a copper compound, a zinc compound, and at least one compound selected from the group consisting of aluminum, zirconium, magnesium a rare earth and mixtures thereof.

The copper content of the catalyst can vary over a wide range for example, from about 10 percent by weight to about 80 percent by weight, calculated as the oxide, basis the total weight of the catalyst. However, for an optimal combination of initial catalyst activity and catalyst stability, a copper content in the range of from about 25 percent by weight to about 75 percent by weight, calculated as the oxide, is preferred, especially from about 30 percent by weight to about 70 percent by weight, calculated as the oxide. All ratios specified herein are metal atoms unless otherwise noted.

The zinc content of the catalyst is typically in the range of from about 10 percent by weight to about 80 percent by weight, calculated as the oxide, basis the total weight of the catalyst. Preferably, the zinc content of the catalyst is in the range of from about 15 percent by weight to about 75 percent by weight, calculated as the oxide, especially from about 20 percent by weight to about 70 percent by weight, calculated as the oxide. The ratio of zinc to copper in the catalyst is generally in the range of from about 1:5 to about 5:1, and preferably in the range of from about 1:4 to about 2:1.

The catalyst additionally comprises at least one compound selected from the group consisting of aluminum, zirconium, magnesium, a rare earth and mixtures thereof.

When a rare earth compound is utilized, the rare earth content of the catalyst is typically in the range of from about 0.1 percent by weight to about 20 percent by weight, calculated as the oxide, basis the total weight of the catalyst. Preferably, the rare earth content of the catalyst is in the range of from about 0.2 percent by weight to about 15 percent by weight, calculated as the oxide, especially from about 0.3 percent by weight to about 10 percent by weight, calculated as the oxide.

As used herein, the terms "rare earth" and "lanthanide" refer to the series of elements with atomic numbers ranging from 57 (lanthanum) through 71 (lutetium). With regard to the rare earth (lanthanide) series, mixed metals are readily available commercially. For purposes of the present invention, the rare earth is selected from the group consisting of praseodymium, neodymium, yttrium, lanthanum, samarium, thorium, cerium and mixtures thereof, with lanthanum being preferred.

When the catalyst contains aluminum, the aluminum content of the catalyst is typically in the range of from about 0.05 percent by weight to about 30 percent by weight, calculated as the oxide, basis the total weight of the catalyst. Preferably, the aluminum content of the catalyst is in the range of from about 0.4 percent by weight to about 20 percent by weight, calculated as the oxide, especially from about 0.6 percent by weight to about 10 percent by weight, calculated as the oxide.

When the catalyst contains zirconium, the zirconium content of the catalyst is typically in the range of from about 0.05 percent by weight to about 30 percent by weight, calculated as the oxide, basis the total weight of the catalyst. Preferably, the zirconium content of the catalyst is in the range of from about 0.4 percent by weight to about 20 percent by weight, calculated as the oxide, especially from about 0.6 percent by weight to about 10 percent by weight, calculated as the oxide.

When the catalyst contains magnesium, the magnesium content of the catalyst is typically in the range of from about 0.05 percent by weight to about 30 percent by weight, calculated as the oxide, basis the total weight of the catalyst. Preferably, the magnesium content of the catalyst is in the range of from about 0.4 percent by weight to about 20 percent by weight, calculated as the oxide, especially from about 0.6 percent by weight to about 10 percent by weight, calculated as the oxide.

When mixtures of a rare earth and/or aluminum and/or zirconium and/or magnesium are utilized, the total amount present in the catalyst is typically in the range of from about 0.05 percent by weight to about 30 percent by weight, calculated as the oxide, basis the total weight of the catalyst. Preferably, the total amount present in the catalyst is in the range of from about 0.4 percent by weight to about 20 percent by weight, calculated as the oxide, especially from about 0.6 percent by weight to about 10 percent by weight, calculated as the oxide.

In one embodiment, the catalyst comprises copper, zinc and zirconium. In another embodiment, the catalyst comprises, copper, zinc and aluminum. In another embodiment, the catalyst comprises copper, zinc, aluminum and zirconium. In another embodiment, the catalyst comprises, copper, zinc and a rare earth. In another embodiment, the catalyst comprises copper, zinc, magnesium and a rare earth.

Various procedures can be utilized to prepare the catalysts of the present invention. For example, individual solutions of the metals may be prepared and mixed together followed by the addition of an aqueous alkaline solution. Alternatively, a first aqueous solution comprising a copper or zinc salt and a second solution comprising a soluble base and at least one soluble salt of at least one second metal can be prepared, and these two solutions are then added simultaneously to a vessel containing water. In a preferred embodiment, the catalysts are prepared by co-precipitating from aqueous solution thermally decomposable compounds of copper, zinc, and rare earth and/or aluminum and/or zirconium and/or magnesium, washing the precipitate and calcining the precipitate to give the metal oxides. The catalyst precursor is subjected to a reduction treatment to give the active catalyst.

It is understood that the catalyst is usually handled and stored in the form of its precursor, which indeed is referred to in commerce as the "catalyst", although it is not the catalyst in the strict sense of the agent taking part in chemical reactions such as hydrogenation of methyl esters. Reduction of the precursor to the catalyst is normally carried out by the operator of the chemical process. The precursor may be in shapes, e.g., pellets, as required by the user of the catalyst, or may be in its condition before the shaping operation, e.g., as powder or lightly compressed powder.

The initial form in which the copper, zinc and rare earth and/or aluminum and/or zirconium and/or magnesium are employed is the oxide, although compounds which are readily converted to the oxide, e.g., the corresponding metal carbonates, are also suitable initially employed as these are converted to the oxide during pretreatment subsequent to the formation of the initially prepared catalyst composition. Pretreatment of the catalyst in hydrogen and operation of the catalyst in the reaction environment will cause at least partial reduction of some of the metals, such as copper, to lower oxidation states, and it is intended that catalysts with these reduced states will fall within the scope of this invention.

In the method of making the catalyst the reaction conditions for the precipitation should be carefully controlled. The temperature for the precipitation is preferably in the range of from about 20° C. to about 100° C., preferably from about 50° C. to about 85° C., and the pH during the precipitation process is maintained between about 5.5 and about 7.5, preferably between about 6.0 to about 7.0 and more preferably, between about 6.3 and about 6.7. The precipitating agent will be an alkali metal or an ammonium carbonate solution. The precipitate thus obtained is a mixture of carbonates, basic carbonates, oxides, hydrated oxides and hydroxides. The precipitate is washed, preferably several times with water, aged, reslurried and then dried and calcined, preferably in air at a temperature of from about 200° C. to about 400° C., with a temperature of about 250° C. to about 350° C. being preferred. The drying is carried out at a temperature sufficient to remove the water. This step is conveniently combined with the calcination by a suitable ramping of the temperature from room temperature slowly through the drying temperature, then up to calcination temperature. The calcined material is shaped, for example, by pelleting under pressure using alumina as a binder, or graphite as lubricant. The oxide mixture is pretreated in a hydrogen-containing atmosphere prior to use as a catalyst to bring it to its most active state. Pretreatment is accomplished by contacting the catalyst with a stream of hydrogen, or of hydrogen mixed with an inert gas or diluent at a temperature ranging from about 100° C. to about 400° C. Suitable diluent gases for the activating gas mixture include nitrogen, the noble gases and mixtures thereof.

In a preferred embodiment, an aqueous solution of copper, zinc and lanthanum salts is employed. Preferably utilized are copper nitrate, zinc nitrate, and lanthanum nitrate. A second solution of alkali metal or preferably, ammonium carbonate is prepared. The two solutions are heated to a temperature of about 20° C. to about 85° C. and simultaneously metered into the precipitation container at rates such that the pH in the precipitation container is maintained between 5.5 and 7.5. Additional water may be used either initially in the precipitation container or added concurrently with the salt solution and precipitation solution. The resulting precipitate is thoroughly washed, dried, calcined at about 300° C. and activated in hydrogen at temperatures ranging from about 100° C. to about 400° C.

In the process of the present invention, one or more detergent range methyl esters is contacted and reacted with hydrogen in the presence of the above-described catalyst in a reactor. The reactor may be a trickle bed reactor, fixed bed gas-solid reactor, packed bubble column reactor, continuously stirred tank reactor or a slurry phase reactor. The process may be carried out batchwise or in continuous fashion. The reaction is carried out in a predominantly liquid phase. As used herein, the term "predominantly liquid phase" refers to a reaction in which greater than 50%, and approaching 100% of the reaction mixture (other than hydrogen) is in the liquid phase.

The reaction temperatures are typically in the range of from about 170° C. to about 250° C., preferably in the range of from about 190° C. to 240° C., and more preferably in the range of from about 205° C. to 230° C. With respect to the reaction temperatures, it is important to ensure that the temperature does not exceed 250° C. At temperatures greater than 250° C., the paraffin make increases to unacceptable levels. The reaction pressures are typically in the range of from about 300 psig to about 2000 psig, preferably in the range of from about 400 psig to about 1500 psig, and more preferably in the range of from about 500 psig to about 1000 psig. Operation at these low reaction pressures is possible due to the high activity and selectivity of the catalysts. The molar ratio of hydrogen to methyl ester in the process of the present invention is in the range of from about 20:1 to about 700:1, preferably from about 50:1 to about 650:1, and more preferably, from about 100:1 to about 600:1. The process is generally carried out at a weight hourly space velocity (WHSV) in the range of from about 0.1 hr$^{-1}$ to about 5 hr$^{-1}$, preferably in the range of from about 0.1 hr$^{-1}$ to about 3 hr$^{-1}$. The time period required for reaction will vary according to the temperature utilized, the molar ratio of hydrogen to methyl ester, and the partial pressure of hydrogen.

The products produced by the present process include fatty alcohols, wax esters, traces of paraffins and unreacted methyl esters. The products are typically separated by conventional means such as, for example, distillation, extraction, filtration, crystallization, and the like. The desired fatty alcohol products are then utilized in various applications, such as, for example, detergents such as laundry powders, laundry liquids, etc. and personal care products such as shampoos, etc.

An advantage of the present process is the conversion, i.e., greater than at least about 80 mole %, and approaching 100%, basis methyl ester, as well as the selectivity to alcohols, i.e., greater than about 95 mole %, and approaching 100%. As used herein "selectivity" is understood to refer to the selectivity following separation of wax esters, i.e., myristyl myristate, which are recycled. The process also has advantages in that it produces very pure alcohols with very low levels of paraffins at relatively low hydrogen to feed ratios.

The ranges and limitations provided in the present specification and claims are those which are believed to particularly point out and distinctly claim the present invention. It is, however, understood that other ranges and limitations which perform substantially the same function in substantially the same manner to obtain the same or substantially the same result are intended to be within the scope of the present invention as defined by the specification and claims.

The invention is further described with reference to the following examples, which are intended to illustrate certain aspects of the invention, without limiting its broader scope.

ILLUSTRATIVE EMBODIMENTS

EXAMPLE 1

Catalyst Preparation

A solution of mixed nitrates, 96 grams (0.41 mole) of cupric nitrate, 60 grams (0.2 mole) zinc nitrate, 3.3 grams (0.008 mole) lanthanum nitrate in one liter of water was heated to 85° C. and placed in a dish and funnel. In a second funnel was placed a hot 50° C. 1 molar solution of ammonium carbonate of sufficient quantity to provide an excess over the metal nitrates. Two solutions were added simultaneously over a period of about 20 minutes to a vessel containing 1 liter of vigorously stirred distilled water at 65° C. The rates of addition were adjusted so as to maintain the pH of the mixture at about pH equal to about 6.5. After the addition had been completed the slurry was aged at 85° C. for 20 minutes and then allowed to settle and washed 5 times by decantation and reslurrying before being filtered and dried. The mixed carbonates were then calcined at 300° C. for 4 hours. The resulting oxide material was compressed isostatically at 20,000 lbs. and then crushed and sieved.

EXAMPLE 2

The catalyst preparation procedure for Example 1 was followed, except that 3.47 g (0.008 mole) cerous nitrate was utilized in place of the lanthanum nitrate.

EXAMPLE 3

The catalyst preparation procedure for Example 1 was followed, except that 3.00 g (0.008 mole) zirconyl nitrate was used in place of the lanthanum nitrate.

EXAMPLE 4

The catalyst preparation procedure for Example 1 was followed, except that 2.2 g (0.009 mole) magnesium nitrate hexahydrate was added to the nitrate salt solution.

EXAMPLE 5

A Cu/Zn/Zr catalyst was prepared as in Example 3, the catalyst was then mixed with 10% by weight of Catapal D alumina (marketed by Vista Chemical Corporation) and a small amount of acetic acid as a peptizing agent. The mixture was mulled, then extruded and calcined as described in Example 1.

EXAMPLE 6

The catalyst preparation procedure for Example 1 was followed, except that 120 g (0.55 moles) copper nitrate was used, and the lanthanum nitrate as replaced with 12.0 g (0.3 moles) aluminum nitrate nonahydrate.

Catalyst Testing

The catalytic testing was conducted in a typical laboratory scale reactor. The reactor tube used was constructed of 316 stainless steel and included a thermowell. The tube had an outer diameter of 1 inch and an inner diameter of 0.6 inches. An equal volume of silicon carbide, (60–80 mesh) was mixed with 20.00 g of catalyst and centered in the reactor tube between two beds of enough 20 mesh silicon carbide to fill the reactor. The silicon carbide was used as a diluent. The reactor tube was placed in a four-zone furnace equipped with controlling thermocouples and its fittings were tightened. A multi-point thermocouple was inserted in to the thermowell to allow precise monitoring of the temperatures inside the reactor tube.

The catalyst was reduced by initiating a 10.0 L/Hr flow of approx. 5% hydrogen in nitrogen at a unit pressure of 135 psig. The reactor was heated at a rate of 60° C./Hr to 200° C. The catalyst was held at 200° C. for 17 hours. While maintaining the same flow rate, the catalyst was next reduced with hydrogen for an additional 8 hours.

After reduction, the unit pressure was raised to the desired pressure, (e.g. 600 psig) by adjusting a backpressure regulator. The hydrogen flow was adjusted to the desired flow rate. The reactor temperature was adjusted to the desired setpoint and the catalyst bed temperatures were allowed to equilibrate before the feed was introduced at the desired feed rate. The feed was stored under nitrogen and, if necessary, heated to a temperature above its melting point before being pumped to the reactor through heated insulated lines to insure proper flow. Typical operating conditions investigated were; temperatures of 150°–260° C.; WHSV of 0.1 to 5 per hour; molar hydrogen to feedstock ratios of between 20:1 and 1000:1; and unit pressures between 200 and 2000 psig. Samples of the feed and products were analyzed by GC, NMR, IR, Mass Spectroscopy and elemental analysis.

The results for hydrogenation of pure methyl tetradecanoate (methyl myristate) are shown in Table 1.

TABLE 1

Catalyst Performance

| Temp. (°C.) | H₂: Feed | Conversion (% m) | Alcohol (% m) | Paraffin (% m) | Wax (% m) | Purity (% m) |
|---|---|---|---|---|---|---|
| Example 1*: | | | | | | |
| 204 | 125:1 | 97.3 | 75.8 | 0.4 | 23.8 | 95.9 |
| 221 | 125:1 | 99.7 | 84.8 | 0.6 | 14.4 | 98.8 |
| 227 | 200:1 | 99.9 | 86.9 | 1.0 | 12.5 | 98.6 |
| Example 2*: | | | | | | |
| 204 | 125:1 | 99.1 | 63.4 | 0.04 | 36.5 | 98.4 |
| 227 | 200:1 | 99.9 | 86.5 | 0.7 | 12.8 | 99.1 |
| Example 3*: | | | | | | |
| 205 | 125:1 | 99.0 | 73.9 | 0.1 | 26.0 | 98.4 |
| 227 | 200:1 | 99.9 | 87.3 | 0.8 | 11.9 | 98.9 |
| Example 4*: | | | | | | |
| 205 | 125:1 | 99.4 | 70.7 | 0.1 | 28.9 | 98.5 |
| 228 | 200:1 | 99.9 | 90.1 | 0.9 | 8.9 | 98.8 |
| Example 5*: | | | | | | |
| 204 | 125:1 | 99.9 | 87.0 | 0.6 | 12.4 | 99.3 |
| 227 | 200:1 | 99.9 | 93.7 | 1.4 | 4.7 | 98.2 |
| Example 6*: | | | | | | |
| 205 | 125.1 | 99.9 | 87.0 | 0.6 | 12.4 | 99.3 |
| 222 | 125.1 | 99.9 | 93.7 | 1.4 | 4.7 | 98.2 |

*WHSV = 0.4, pressure = 600 psig.

As can be seen in Table 1 the present process results in conversions greater than 97 mole percent and product purities (of alcohol) greater than 95 mole percent. It can also be seen that the product yields of alcohol are greater than 95 mole percent, and that the paraffin make is less than 2 mole percent.

What is claimed is:

1. A process for the direct hydrogenation of methyl esters which comprises contacting and reacting one or more detergent range methyl esters with hydrogen under predominantly liquid phase hydrogenation conditions in the presence of a catalyst comprising a copper compound, a zinc compound and at least one compound selected from the group consisting of aluminum, zirconium, magnesium, a rare earth and mixtures thereof.

2. The process of claim 1 wherein said detergent range methyl ester is selected from the group consisting of methyl decanoate (methyl caprate), methyl dodecanoate (methyl laurate), methyl tetradecanoate (methyl myristate), methyl hexadecanoate (methyl palmitate), methyl octadecanoate, methyl octadecenoate and mixtures thereof.

3. The process of claim 2 wherein said detergent range methyl ester is methyl myristate.

4. The process of claim 1 wherein said catalyst contains from about 10 percent by weight to about 80 percent by weight, calculated as the oxide, basis the total weight of the catalyst, of copper.

5. The process of claim 1 wherein said catalyst contains from about 10 percent by weight to about 80 percent by weight, calculated as the oxide, basis the total weight of the catalyst, of zinc.

6. The process of claim 1 wherein said catalyst contains copper, zinc and a rare earth compound.

7. The process of claim 6 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.1 percent by weight to about 20 percent by weight, calculated as the oxide, basis the total weight of the catalyst, of rare earth.

8. The process of claim 7 wherein said rare earth is selected from the group consisting of selected from the group consisting of praseodymium, neodymium, yttrium, lanthanum, samarium, thorium, cerium and mixtures thereof.

9. The process of claim 8 wherein said rare earth is lanthanum.

10. The process of claim 8 wherein said rare earth is cerium.

11. The process of claim 1 wherein said catalyst contains copper, zinc and aluminum.

12. The process of claim 11 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of aluminum.

13. The process of claim 1 wherein said catalyst contains copper, zinc and zirconium.

14. The process of claim 13 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of zirconium.

15. The process of claim 1 wherein said catalyst contains copper, zinc, zirconium and aluminum.

16. The process of claim 15 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of zirconium, and from about 0.05 percent by weight to about 30 percent by weight, basis the total weight of the catalyst, of aluminum.

17. The process of claim 1 wherein said catalyst contains copper, zinc, magnesium and a rare earth compound.

18. The process of claim 17 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of magnesium, and from about 0.1 percent by weight to about 20 percent by weight, calculated as the oxide, basis the total weight of the catalyst, of rare earth.

19. The process of claim 18 wherein said rare earth is selected from the group consisting of selected from the group consisting of praseodymium, neodymium, yttrium, lanthanum, samarium, thorium, cerium and mixtures thereof.

20. The process of claim 1 wherein said process is carried out at a temperature in the range of from about 170° C. to about 250° C. and a pressure in the range of from about 300 psig to about 2000 psig.

* * * * *